United States Patent
Weatherford et al.

[11] Patent Number: 5,527,294
[45] Date of Patent: Jun. 18, 1996

[54] SHIELDED SYRINGE

[75] Inventors: Cheryl A. Weatherford, Oceanside; E. Craig Wilhelm, Laguna Niguel, both of Calif.

[73] Assignee: Safety 1st, Laguna Niguel, Calif.

[21] Appl. No.: 140,786

[22] Filed: Oct. 20, 1993

Related U.S. Application Data

[63] Continuation-in-part of Ser. No. 63,246, May 18, 1993, Pat. No. 5,290,256.

[51] Int. Cl.⁶ .................................................. A61M 5/32
[52] U.S. Cl. ........................... 604/198; 604/263; 604/110
[58] Field of Search .................................... 604/198, 263, 604/110, 187, 192, 195

[56] References Cited

U.S. PATENT DOCUMENTS

| | | | |
|---|---|---|---|
| 5,057,079 | 10/1991 | Tiemann et al. | 604/110 |
| 5,197,953 | 3/1993 | Colonna | 604/198 X |
| 5,201,708 | 4/1993 | Martin | 604/198 X |
| 5,259,841 | 11/1993 | Hohendorf et al. | 604/110 |

*Primary Examiner*—John D. Yasko
*Attorney, Agent, or Firm*—Walter A. Hackler

[57] ABSTRACT

A shielded syringe includes a cylindrical syringe barrel having an interior chamber a needle secured at one end of said barrel and a plunger slidably received within the interior chamber A sheath for preventing contact with said needle is provided with the sheath being slidably disposed on said cylindrical syringe barrel and movable therealong from a closed position surrounding said needle to an open position exposing said needle A locking system for releasably locking the sheath in both the open and closed positions, includes a tab disposed on an inside surface of said sheath an elongate strip member having one and thereof secured to said cylindrical syringe barrel and a pair of berms thereon for engaging said tab. A spring is provided for urging said tab against one of said pair of berms when the sheath is in the open position and in the closed position.

7 Claims, 2 Drawing Sheets

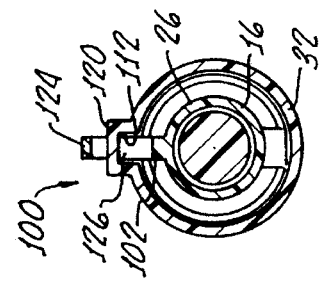
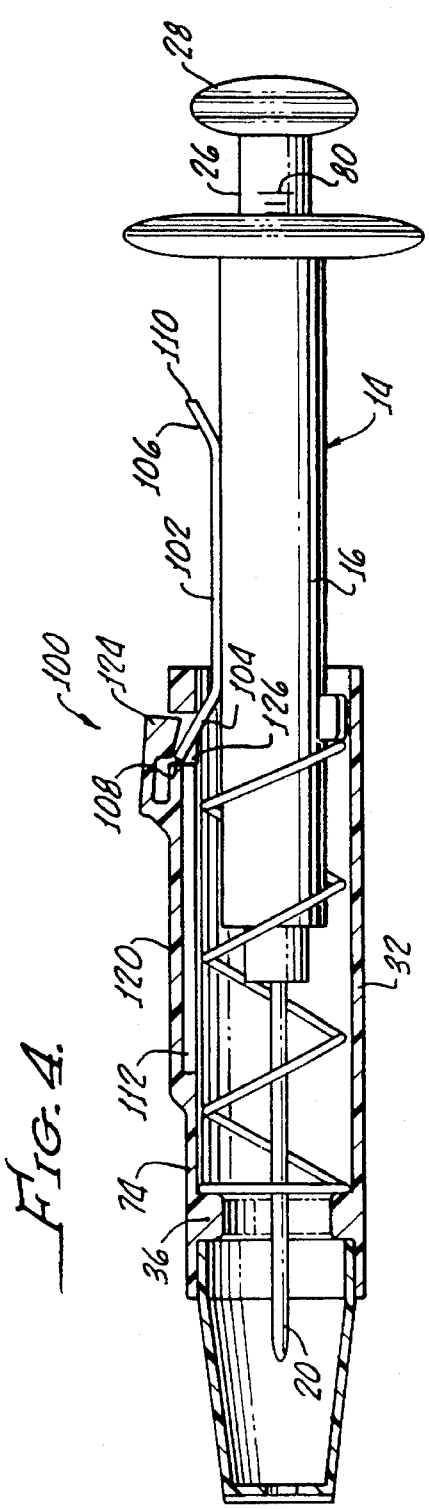
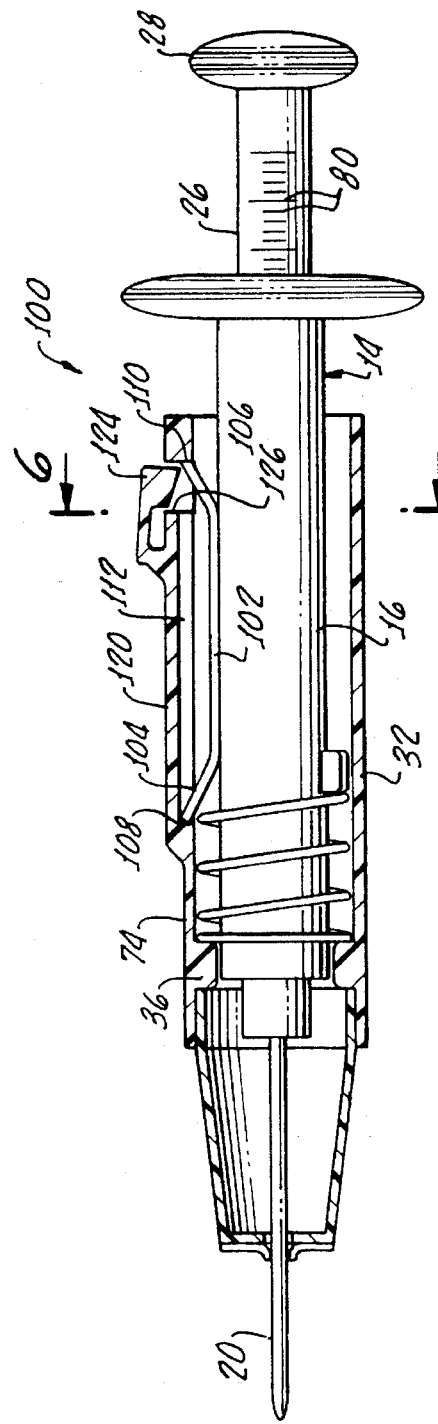

SHIELDED SYRINGE

This application is a continuation-in-part of U.S. Ser. No. 08/063,246, filed May 18, 1993, now U.S. Pat. No. 5,290,256.

The present invention generally relates to surgical/medical devices and more particularly to a shield assembly in combination with a syringe or the like for the prevention of undesirable exposure to contaminated, or used, syringe needles or the like.

Most medical procedures—both medical and dental—require the use of hypodermic syringes, either for the injecting of anesthetics, drugs, antibiotics, and/or other medical fluids into a patient's body or for the extraction of fluid samples from the patient's body. Surgical/medical devices utilized in such procedures include, for example, but are not limited to: insulin syringes, tuberculin syringes, phlebotomy devices, vacutainers, catheters, and scalpels.

Hypodermic syringe needles, for example, need to be kept sterile prior to use and are, of necessity, extremely sharp. Consequently, such needles are commonly provided with removable and replaceable needle caps which, when installed on the needles, keep the needles sterile (or at least clean). Installed needle caps also protect users and handlers of the needles or hypodermic syringes on which the needles are installed, against accidental needlesticks. Thus, when syringe needles are being installed onto or removed from hypodermic syringes and when the syringes with needles installed are not in actual use, the capping of the needles is preferred for hygienic and safety reasons.

For many years blood-borne diseases have been known to be transmittable from an infected individual to a non-infected individual by certain contact with the infected individual's blood; for example, if the infected individual's blood enters an open cut, sore or wound on the previously non-infected individual's body. Surgeons and other medical personnel who may contact a patient's or injured person's blood typically (except, perhaps, in cases of serious emergency) wear rubber surgical gloves which not only protect the patient or injured person against infection by germs and bacteria from the treating person's hands, but also protect the treating person from being infected, through cuts on the hands, from possibly being infected by the patient's or injured person's blood.

Needlesticks by hypodermic syringe needles used on patients (or other individuals) are another means whereby blood-borne diseases can be transmitted from a patient to an individual treating the patient. In this regard, surgical gloves usually provide negligible protection for the wearers against accidental needlesticks.

Until a few years ago, the principal risk to health care professionals from accidental needlesticks was generally considered to be the contracting of hepatitis from an infected patient. As is well-known, Hepatitis B is still one of the major unresolved infectious disease problems of our time. it remains a threat to the public as well as to the health care community. the other hand, the frequent capping and uncapping of hypodermic syringe needles increase the risk of accidental needlesticks for the individuals performing the capping operations.

Moreover, the risk of an individual receiving an accidental needlestick during the needle recapping operation is greatly increased when the individual doing the recapping is physically or mentally distracted by other matters, such as the course of a medical treatment or operation and when the needle cap is held in one hand while the needle is inserted by the other hand into the cap (or while the manually-held cap is installed over the needle).

It is, therefore, a principal objective of the present invention to provide a shielded syringe or shield assembly for a syringe which is convenient to use and requires no awkward movement in its use.

SUMMARY OF THE INVENTION

A shielded syringe in accordance with the present invention generally includes a cylindrical syringe barrel having an interior chamber and a needle secured at one end of the barrel with a plunger slidably received within the interior chamber.

In combination therewith, or suitable for use in conjunction with the cylindrical syringe barrel, needle, and plunger, is a sheath which provides means for preventing contact with the needle. The sheath is selectively disposed over the cylindrical syringe barrel and movable therealong from a closed position surrounding the needle to an open position exposing However, with the onset of AIDS (acquired immunodeficiency syndrome)—a fatal, blood-borne disease for which no vaccination against nor cure for is presently known—a few years ago, the health risks associated with accidental needlesticks by used hypodermic syringe needles have escalated dramatically. In this regard, the sharing of hypodermic needles by users of controlled substances is well known to be a major factor in the rapid spread of AIDS. Thus, in spite of the great care exercised by health care professionals, accidental needlesticks by used hypodermic needles have been responsible for contracting AIDS. For example, in one widely-publicized case, a doctor reportedly contracted AIDS as a result of receiving a needlestick from an unseen and apparently improperly disposed hypodermic syringe needle. As another example, in a recent, reverse-twist case, a dental patient is believed to have contracted AIDS from a dentist who reportedly had AIDS, the theory (at least presently) being that the dentist may have experienced an accidental needlestick from the hypodermic syringe needle subsequently used to administer an anesthetic to the patient.

The risk of contracting or transmitting AIDS via accidental needlesticks presents health care professionals (as well as non-professionals, such as family members, who have to give injections, for example, insulin injections, to others) with a serious dilemma. On the one hand, the capping of hypodermic syringe needles whenever the associated syringe is not actually being used or when disposing of the needle (or entire syringe, as the case may be) is obviously highly desirable to prevent accidental needlesticks and the health risks associated therewith. Yet, on the needle. Locking means are provided for releasably locking the sheath means in both the open and closed positions with the locking means comprising a tab disposed on an inside surface of the sheath and an elongate strip member having one end thereof secured to the cylindrical syringe barrel and a pair of berms thereon for engaging the tab. Thus, the structure of the present invention provides the convenience of releasably securing the sheath in a position preventing contact with the needle and also in a position enabling access to the needle so that it may be used in a conventional manner.

Spring means are provided for urging the tab against one of the pair of berms when the sheath means is in open position and also in the closed position.

This is an important feature of the present invention in that a single spring is utilized in engaging a locking of the sheath in both an open and closed position. From a manufacturing point of view, this has significant economic advantages.

The spring means provides sufficient force to move the sheath means to the closed position upon disengagement of the tab from the berm holding the sheath in the open position. Further, the locking means may further include button means for manually disengaging the tab from either of the berms. Button means may be disposed on another end of the elongate surface at a position accessible when the sheath is either in a closed or an open position.

To facilitate use of the shielded syringe when the sheath is in an open position, the plunger may include indicia thereon for enabling the user to determine the amount of fluid within the cylindrical syringe barrel.

An alternative embodiment of the present invention provides a shield assembly for a syringe having a cylindrical syringe barrel, a needle secured to one end of the barrel, and a plunger slidably disposed within an internal chamber of the cylindrical syringe. In this embodiment the tab is disposed on an outside surface of the sheath and the berms are disposed on the plunger.

This embodiment of the shield assembly includes a sheath for preventing contact with the needle, with the sheath being slidably disposed over the cylindrical syringe barrel and therealong in a closed position surrounding the needle to an open position exposing the needle. Locking means are provided for releasably locking the sheath means in both the open and closed positions, as hereinabove noted, and a spring is provided for urging the cap disposed on the inside surface of the sheath means against one of the pair of berms on the sheath means both in the open position and in a closed position.

BRIEF DESCRIPTION OF THE DRAWINGS

The advantages and features of the present invention will be better understood by the following description when considered in conjunction with the accompanying drawings in which:

FIG. 4 is a cross-sectional view of an alternative embodiment of the present invention showing a sheath in a closed position over a syringe needle;

FIG. 5 is a cross-sectional view of the syringe shown in FIG. 4 with the sheath in an open position exposing the needle; and FIG. 6 is a cross-sectinal view taken allong line 6—6 of FIG. 5.

DETAILED DESCRIPTION

Figure 1:
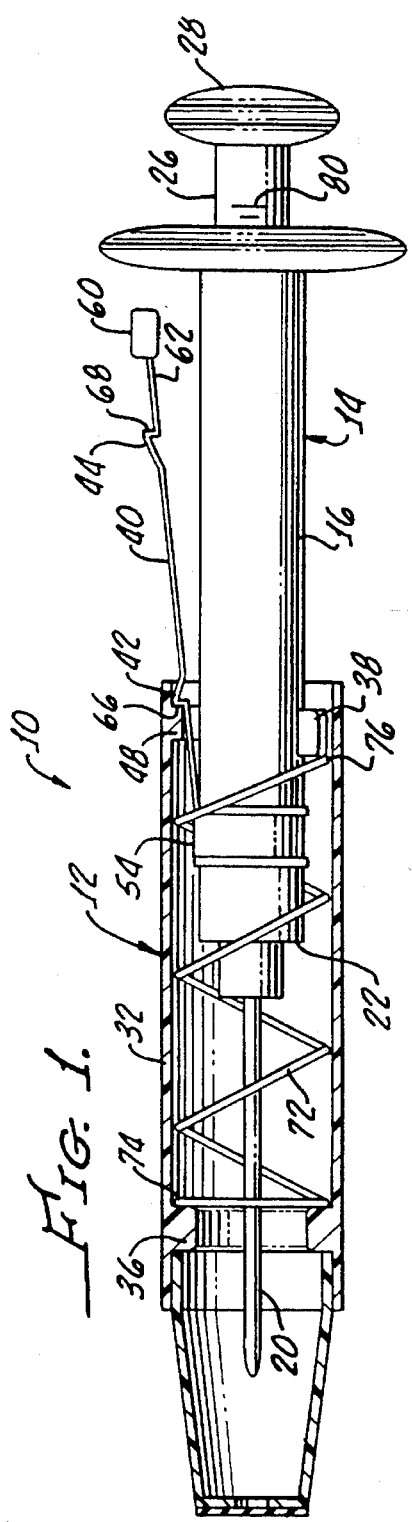
FIG. 1 is a cross-sectional view of the shielded syringe, in accordance with the present invention, showing a sheath in a closed position over a syringe needle.

In FIG. 1, there is shown a syringe 10 in accordance with the present invention which also includes a shield assembly 12, a cylindrical syringe barrel 14 in an interior chamber 16, a needle 20 which is adhered to one end 22 of the barrel 14, and a plunger 26 slidably received within the interior chamber 16 of the barrel 14.

The syringe barrel 14 and needle 20 may be of any conventional design with the needle 20 attached to the front 22 of the barrel 14 by any manner known in the art.

A barrel 14, needle 20 and plunger 26 may be formed from any conventional material suitable for needle apparatus, and the plunger 26 is sized and designed in a conventional manner for dispensing a fluid (not shown) from the interior chamber 16 of the barrel 14 through the needle 20 in a conventional manner when the plunger 26 is operated through a handle 28.

The sheath assembly 12, which also may be formed from any conventional material suitable for use in a medical device, includes a sheath 32 which is sized to surround the barrel 14 and which provides a means for preventing contact with the needle 20. As hereinafter described in greater detail, the sheath 32 is slidably disposed over the barrel 14 and is stabilized thereon by bearing members 36.

Figure 2:
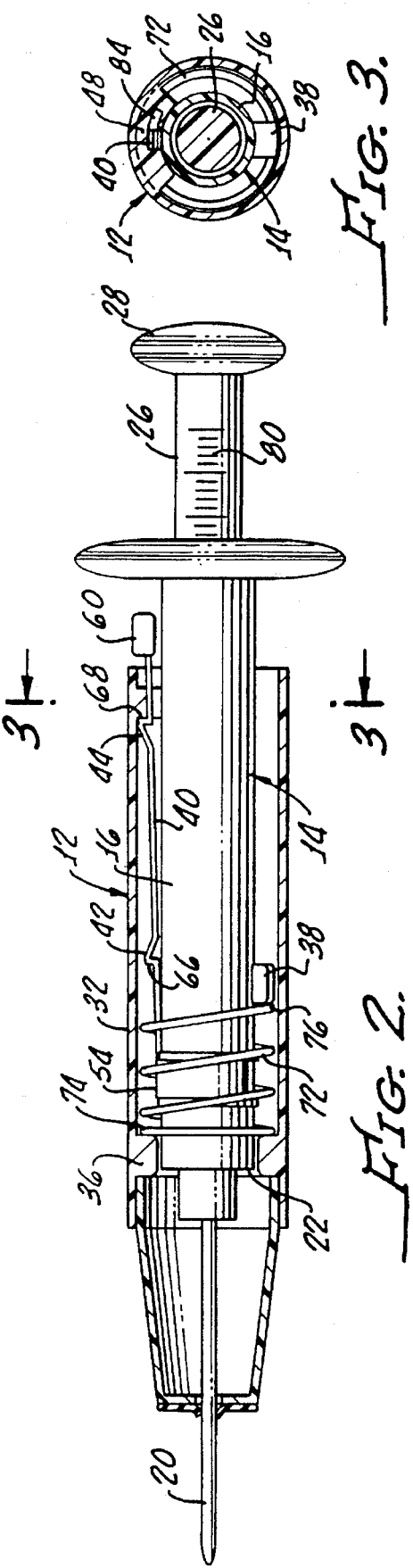
FIG. 2 is a cross-sectional view similar to FIG. 1 with the sheath in an open position exposing the needle.

The sheath 32 is movable from a closed position surrounding the needle 20, as shown in FIG. 1, to an open position exposing the needle 20, as shown in FIG. 2. An elongate strip member 40, along with a forward berm 42 and rear berm 44, and a tab 48, disposed on an inside surface 50 of the sheath 32 provide a means for releasably locking the sheath 32 in both the open position, as shown in FIG. 1, and closed position, as shown in FIG. 2. The elongate strip member 40 includes one end, which may include a band 54, secured to the barrel 14 in a manner causing the elongate member 40 to be urged away from the barrel and a button 60 is provided on another end 62 with the elongate member 40 to provide the means for manually disengaging the tab 48 from either of the berms 42, 44.

Each of the berms 42, 44 has a flat face 66, 68 opposing one another and sized for engagement with the tab 48. The berms 42, 44 are attached, or molded into, the elongate strip 40 in a spaced apart relationship as shown in FIGS. 1 and 2, so that when the tab 48 engages the flat face 66 of the berm 42, the sheath 32 is in a closed position, as shown in FIG. 1, and when the tab 48 engages the flat face 68 of the berm 44, the sheath 32 is locked into the open position, as shown in FIG. 2.

Importantly, a spring 72, which may be a coil spring, is disposed within the sheath 32 and fixed thereto at one spring end 74 and fixed to the barrel 14 at another end 76 of the spring 72.

The spring is sized and shaped so that the expansive force thereof is sufficient to move the sheath 32 from the open position, as shown in FIG. 2, to the closed position, as shown in FIG. 1, when the button 60 is depressed, thus releasing the tab 48 from the berm 44.

The spring is further sized and attached to the sheath 32 at one end 74 and the barrel 14 at another end 76 for enabling the spring 72 to exert an expansion force to urge the tab 48 against the berm 42 when the sheath 32 is in an open position and a contractive force to urge the tab 48 against the rear berm 44 when the sheath 32 is in the closed position. Thus, only one spring is necessary to provide a positive locking of the sheath 32 in both the open and closed positions.

Since the sheath 32, in the open position, substantially encircles the barrel 14, it may be made of a transparent material enabling visual observation of fluid disposed within the barrel 14.

On the other hand, if the sheath 32 is made from an opaque material, then indicia 80 in the form of a graduated scale may be provided along the plunger 26 for enabling the user to determine an amount of fluid within the cylindrical syringe barrel 14.

Figure 3:
FIG. 3 is a cross-sectional view of the syringe showing a separate locking system.

As shown in FIG. 3, a slot 84 provides an independent means for locking the sheath 32 in the closed position.

The slot 84 enables the barrel 14 with the strip 40 to be rotated to a position so that pressing of the button 60 will not release the tab 48 from the berms 42, 44 with the sheath 32 in the closed position.

Turning now to FIGS. 4, 5 and 6, there is shown an alternative embodiment 100 in accordance with the present invention wherein like reference numerals or characters refer to identical or corresponding parts to the embodiment 10 hereinabove described.

A sheath 42 is movable from a closed position surrounding the needle 20, as shown in FIG. 4, to an open position exposing the needle 20, as shown in FIG. 5. An elongate strip member 102 may be disposed along the cylindrical syringe barrel 14 and include a forward berm 104 and a rear berm 106 with flat ends 108, 110 thereon for engaging a tab 124 disposed on an outside surface of the sheath 32.

A slot 112 in the sheath 32 enclosed by a cover 120 attached to the sheath provides a means for slidably receiving the forward berm 104 attached thereto, and on an exterior of the sheath 32 is a depressible element 124 which can engage either of the berms 104, 106 through an aperture 126 through the sheath 32 for depressing either of the berms 104, 106 in order to disengage the berms 104, 106 from the tab and enable the shield to slide from an open to a closed position, or vice versa. When in an open position, exposing the needle 20, the sheath is driven to the closed position upon depression of the rear berm 106 by the element 124 through an aperture 126.

Premature or undesired sliding of the sheath 32 to expose the needle 20 is prevented by engagement of the forward berm 104 with the cover 120. Passage of the forward berm 104 past the cover 120 and into the slot 118 is enabled by depressing the forward berm through the use of the element 124.

While the elongate member 102 includes the berms 104, 106 and is disposed on the cylindrical barrel 14 for ease of assembly, the berms 104, 106 may also be formed directly into the barrel 14.

Although there has been hereinabove described a specific arrangement of a shielded syringe and shield assembly in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A shielded syringe comprising:

a cylindrical syringe barrel having an interior chamber;

a needle secured at one end of said barrel;

a plunger slidably received within the interior chamber;

sheath means for preventing contact with said needle, said sheath means being slidably disposed on said cylindrical syringe barrel and movable therealong from a closed position surrounding said needle to an open position exposing said needle;

locking means for releasably locking said sheath means in both the open and closed positions, said locking means comprising a tab disposed on an outside surface of said sheath means and an elongate strip member secured to said cylindrical syringe barrel and a pair of berms thereon for engaging said tab; and spring means for urging said tab against one of said pair of berms when the sheath means is in the open position and in the closed position.

2. The shielded syringe according to claim 1 wherein the berms each comprise a flat face thereon, the flat faces being opposite to one another.

3. The shielded syringe according to claim 2 wherein said spring means is disposed within said sheath means and over said cylindrical syringe barrel and comprises coils with expansion force sufficient to move the sheath means to the closed position upon disengagement of the tab from a berm holding the sheath in the open position.

4. The shielded syringe according to claim 3 wherein said berms are depressible toward the cylindrical syringe barrel and said shielded syringe further comprises means for depressing said berms in order to disengage said berms from the tab.

5. The shielded syringe according to claim 4 further comprising guide means, disposed exterior to said sheath means, for slidably receiving one of said berms.

6. The shielded syringe according to claim 5 further comprising means, defining an aperture in said sheath means, for enabling access to either of said berms by said means for depressing said berm, and said means for depressing said berms is disposed exterior to said sheath means.

7. The shielded syringe according to claim 6 wherein said plunger comprises means defining indicia thereon for enabling a user to determine an amount of fluid within said cylindrical syringe barrel.

\* \* \* \* \*